United States Patent [19]

Higashiizumi et al.

[11] Patent Number: 5,031,625

[45] Date of Patent: Jul. 16, 1991

[54] RECEIVED ULTRASONIC PHASE MATCHING CIRCUIT

[75] Inventors: Takao Higashiizumi; Toru Shimazaki; Keiki Yamaguchi; Yasuro Takiura, all of Tokyo, Japan

[73] Assignee: Yokogawa Medical Systems, Limited, Tokyo, Japan

[21] Appl. No.: 555,487

[22] PCT Filed: Jan. 30, 1989

[86] PCT No.: PCT/JP89/00095

§ 371 Date: Jul. 30, 1990

§ 102(e) Date: Jul. 30, 1990

[87] PCT Pub. No.: WO89/06933

PCT Pub. Date: Aug. 10, 1989

[30] Foreign Application Priority Data

Jan. 29, 1988 [JP] Japan .................................. 63-18773

[51] Int. Cl.[5] .................................................. A61B 8/00

[52] U.S. Cl. ............................. 128/660.01; 324/77 H

[58] Field of Search ............ 128/660.1, 660.7, 661.01; 324/77 H, 77 B, 83 D, 683

[56] References Cited

U.S. PATENT DOCUMENTS

| | | | |
|---|---|---|---|
| 4,542,657 | 9/1985 | Barber et al. | 324/77 H |
| 4,649,392 | 3/1987 | Apostolos | 324/77 H |
| 4,888,746 | 12/1989 | Wurster et al. | 128/660.01 |
| 4,949,312 | 8/1990 | Iwasawa | 128/660.01 |
| 4,951,219 | 8/1990 | Zimmer | 324/77 B |

*Primary Examiner*—Francis Jaworski
*Assistant Examiner*—George Manuel
*Attorney, Agent, or Firm*—Moonray Kojima

[57] ABSTRACT

A received ultrasonic phase matching circuit of the present invention, which utilizes variable delay lines having short delay times as the structural element of variable focus means having a larger aperture and realizes focusing to the regions from the region near the surface of object and to the deeper region thereof, comprises variable attenuators to be controlled individually and variable delay lines having the equal maximum delay times also to be controlled individually to the respective receiving channels forming the maximum aperture for reception of the ultrasonic echoes to form variable aperture by controlling variable attenuators and distribution of delay times for focusing in the aperture using only the variable delay times belonging to such aperture and add and combine the receiving signals delayed by the variable delay lines in the beam steering means.

1 Claim, 2 Drawing Sheets

FIG.3
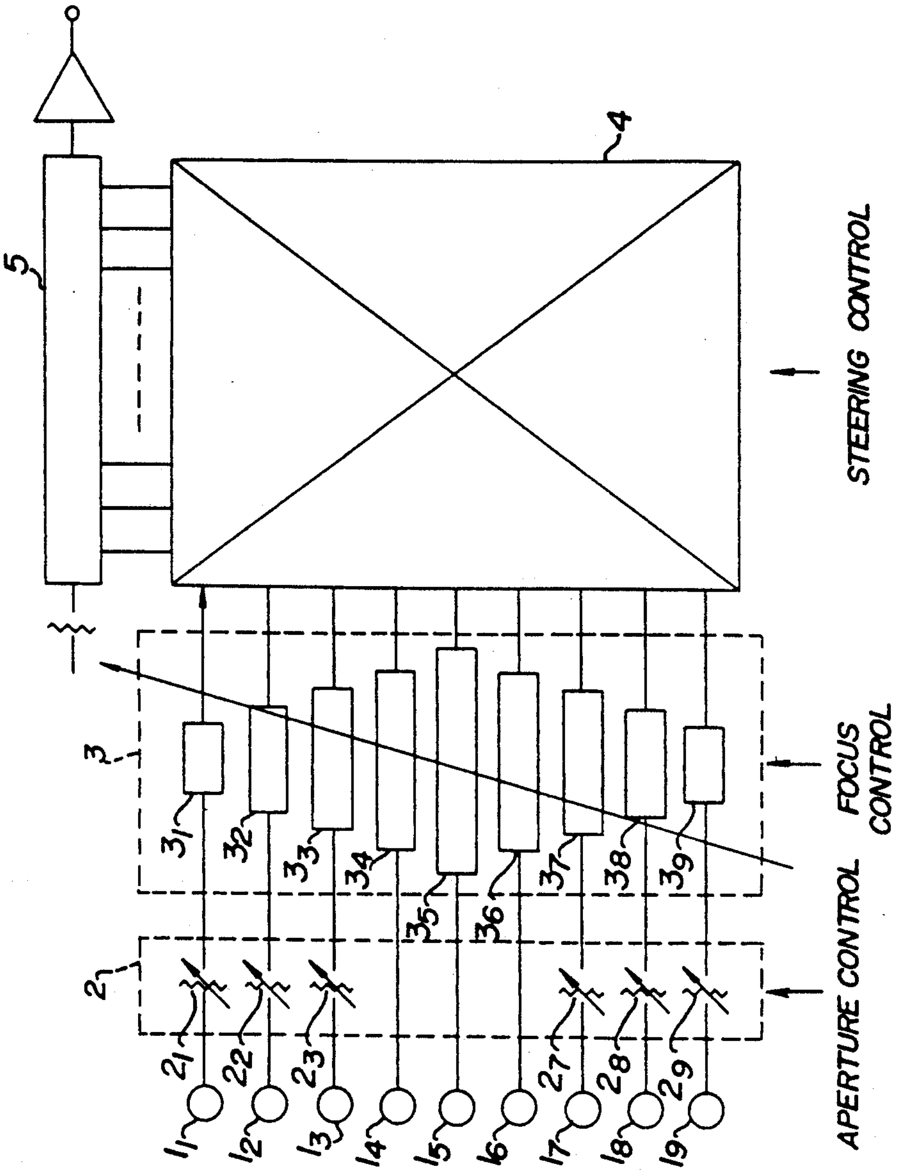
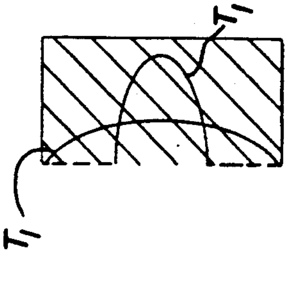
FIG.2A
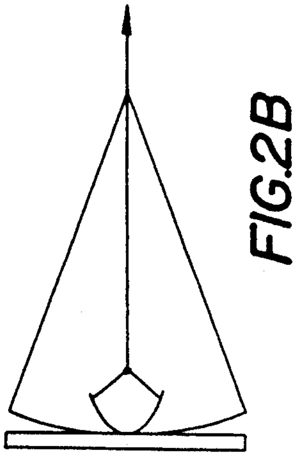
FIG.2B

RECEIVED ULTRASONIC PHASE MATCHING CIRCUIT

TECHNICAL FIELD

The present invention relates to a received ultrasonic phase matching circuit to be used in an ultrasonic diagnostic apparatus and more specifically to a received ultrasonic wave phase matching circuit which continuously changes, during the receiving period, the ultrasonic wave echo receiving focus and aperture.

PRIOR ART

In an ultrasonic diagnostic apparatus, the ultrasonic wave echo receiving focus and aperture are continuously changed to make a resolution of B-mode image high and uniform at the range from the shallow region of object to the deep region thereof depending on the depth of echo generating point while the echo of one sound line is received. This is to obtain uniform and high resolution by making constant a ratio of focal distance and aperture, namely the F number during reception of echo. A prior art of the circuit to realize such function is shown in FIG. 3. In the circuit of FIG. 3, the receiving signals of individual transducer elements of the ultrasonic wave transducer array not illustrated are supplied to a plurality of channels $1_1$-$1_9$ forming the maximum aperture to receive the ultrasonic wave echo of the one sound line and the receiving signal of each channel is respectively attenuated by a plurality of variable attenuators $2_1$-$2_9$ forming a variable aperture means 2, delayed by a plurality of variable delay lines $3_1$-$3_9$ forming a variable focus means 3 and is then input to a plurality of input lines of a matrix switch circuit 4. The matrix switch circuit 4 comprises therein a plurality of input lines extending in horizontal and a plurality of output lines extending in vertical, has switches arranged at the intersecting points of these input lines and output lines and is designed to connect the desired input lines to the desired output lines by controlling ON and OFF conditions of respective switches. A plurality of output lines of matrix switch circuit 4 are respectively connected with the taps of a fixed delay line 5 having a plurality of taps. The receiving signals of a plurality of channels can be input to the desired taps of fixed delay line 5 by controlling ON and OFF conditions of the switches of the matrix switch circuit 4. From the output ends of delay line 5, the signals input to respective taps are output with addition of the delay time corresponding to the tap position. Combination of the matrix switch circuit 4 and fixed delay line with taps 5 forms a beam steering means which determines direction of received ultrasonic beam. The variable attenuators $2_1$-$2_9$ of the variable aperture means 2, variable delay lines $3_1$-$3_9$ of the variable focus means 3 and each switch of matrix switch circuit 4 are respectively controlled by the aperture control signal, focus control signal and steering control signal sent from the control circuit not illustrated to determine the aperture, focus and azimuth angle for reception of ultrasonic echoes.

For the reception of ultrasonic wave echo of the one sound line, the aperture means 2 operates to gradually expand the small aperture around the center channel $1_5$ at the beginning of reception to a larger aperture with the aperture control signal, while the variable focus means 3 operates to gradually control the shortest focal distance at the beginning of the reception, namely the longest delay time of the variable delay lines $3_1$-$3_9$ to the longer focal distance, namely the shortest delay time of the variable delay lines $3_1$-$3_9$ with the focus control signal. The matrix switch circuit 4 realizes beam steering in accordance with the direction of sound line of ultrasonic wave echo with the steering control signal. The received ultrasonic wave phase matching circuit of the present invention will be used for any types of ultrasonic diagnostic apparatus of the linear scanning type, sector scanning type and convex scanning type. Namely, in the linear scanning type and convex scanning type ultrasonic diagnostic appartuses, the scanning of ultrasonic beam is realized by sequentially selecting the transducer element group of the ultrasonic probe connected to the channels $1_1$-$1_9$ with the scanning switch and in the sector scanning type ultrasonic diagnostic apparatus, the scanning of ultrasonic beam is realized by controlling the beam steering with the matrix switch 4.

Here, the variable delay line $3_5$ at the center of aperture is the longest among the variable delay lines $3_1$-$3_9$ of the variable focus means 3 and the variable delay line groups $3_4$-$3_1$ and $3_6$-$3_9$ in both sides thereof sequentially become shorter as they become far from the center and thereby forming a variable "convex lens" for the aperture as a whole. The variable delay lines $3_1$-$3_9$ forming the "convex lens" are formed by an LC circuit utilizing the fixed inductance element and variable capacitor but the variable delay line having excellent high frequency characteristic which may be realized by such LC circuit is capable of allowing only five folds in maximum of variable range and providing the maximum delay time of about 1 us. Therefore, the variabale focus means 3 can realize variable range of focus, for example, of 20 mm-100 mm which is insufficient for covering the focus from the region near the surface of the object to the deeper region thereof. Moreover, it is essential to make as larger as possible the maximum value of aperture for obtaining equalized resolution up to the deeper region of object. In this case, however, the shortest focal distance which may be realized by the variable focus means 3 becomes longer and focusing is now impossible for the shallow region of object.

SUMMARY OF THE INVENTION

It is therefore an object of the present invention to provide a received ultrasonic phase matching circuit which utilizes variable delay lines of short delay times as the structural elements of the variable focus means having a larger aperture and realizes uniform focusing from the region near the surface of object to the deeper region thereof.

The received ultrasonic phase matching circuit of the present invention comprises variable attenuators controlled individually and variable delay lines individually controlled to provide the same maximum delay time respectively for a plurality of receiving channels forming the maximum aperture to receive the ultrasonic wave echoes and is characterized in forming a variable aperture by controlling the variable attenuator, forming distribution of delay times for focusing in the aperture using the variable delay line belonging to the aperture and adding and combining the receiving signals delayed by these variable delay lines in the beam stearing means.

BRIEF DESCRIPTION OF THE DRAWINGS

FIG. 2A is a diagram indicating distribution of delay times formed in the aperture by the variable focus means;

FIG. 2B is a diagram indicating the variable range of focus formed by the variable focus means; and FIG. 3 is a conceptional structural diagram of the prior art.

BEST MODE FOR CARRING OUT THE INVENTION

Figure 1:
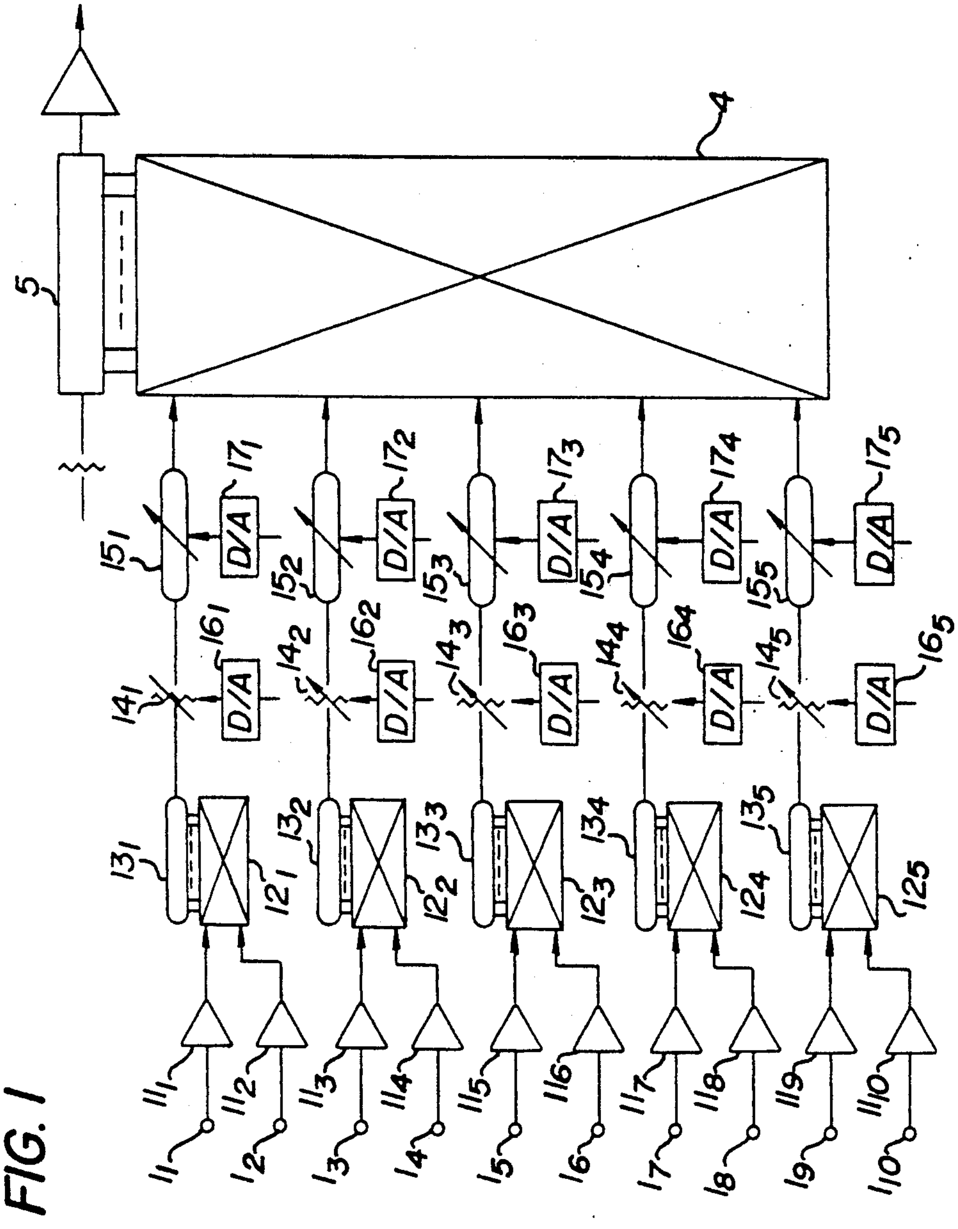
FIG. 1 is a conceptional structural diagram of an embodiment of the present invention.

The conceptional structural diagram of an embodiment of the present invention is shown in FIG. 1. In FIG. 1, the receiving signals of individual transducer elements of ultrasonic trasducer array not illustrated are supplied to a plurality of channels $1_1$–$a_{10}$ forming the maximum aperture in relation to the reception of ultrasonic echoes of the one sound line and the receiving signal of each channel is amplified respectively by the preamplifiers $11_1$–$11_{10}$. Here, the number of channels forming the maximum aperture is set to 10 for convenience of the explanation and it is not limited thereto. The signals amplified by the preamplifiers $11_1$–$11_{10}$ are input to the submatrix switches $12_1$–$12_5$ in pairs and delayed and combined into the one receiving signal in the subdelay lines $13_1$–$13_5$. The output signals of subdelay lines $13_1$–$13_5$ are attenuated by a plurality of variable attenuators $14_1$–$14_5$ forming a variable aperture means, delayed by a plurality of variable delay lines $15_1$–$15_5$ forming a variable focus means and then input respectively to a plurality of input lines of the matrix switch circuit 4. This circuit is similar to that of the prior art. Namely, this matrix switch circuit 4 comprises therein a plurality of input lines extending in horizontal and a plurality of output lines extending in vertical, has switches arranged at the intersecting points of such input lines and output lines and is designed to connect the desired input lines to the selected output lines by controlling the ON and OFF conditions of the switches. A plurality of output lines of matrix switch circuit 4 are respectively connected to the taps of fixed delay line 5 having a plurality of taps. The received signal of a plurality of channels can be input to the desired taps of the fixed delay line 5 by controlling the ON and OFF conditions of the switches of matrix switch circuit 4. From the output ends of delay line 5, the signals input to the taps are output with addition of the delay times corresponding to the tap positions. Combination of matrix switch circuit 4 and fixed delay lines 5 with taps forms the beam steering means which determines direction of the received ultrasonic beam. The variable attenuators $14_1$–$14_5$ of the variable aperture means, variable delay lines $15_1$–$15_5$ of variable focus means and switches of matrix switch circuit 4 are controlled by the control signals applied from the control circuit not illustrated in order to determine aperture, focus and azimuth angle for reception of ultrasonic echoes. The control signals of variable attenuators $14_1$–$14_5$ of variable aperture means are applied individually as the digital signals and are converted to analog signals by the D/A converters $16_1$–$16_5$ for use as the control signal. The control signals of variable delay lines $15_1$–$15_5$ of variable focus means are also applied individually as the digital signals and are converted into analog signals by the D/A converters $17_1$–$17_5$ for use as the control signal. The matrix switch circuit 4 conducts beam steering depending on the direction of sound line of ultrasonic echoes with the steering control signal. Like the prior art, the received ultrasonic phase matching circuit can also be used in common in the linear scanning type, sector scanning type and convex scanning type ultrasonic diagnostic apparatuses.

For the reception of ultrasonic wave echo of the one sound line, the aperture means 2 operates to gradually expand the small aperture around the center channels $1_5$, $1_6$ at the beginning of reception to a larger aperture with the aperture control signal, while the variable focus means 3 operates to gradually control the shortest focal distance corresponding to a small aperture at the beginning of the reception, to the longer focal distance corresponding to the expanded aperture signal.

Here, the variable delay lines $15_1$–$15_5$ of variable focus means have the same maximum delay time and are all structured by the LC circuit utilizing a fixed inductance element and variable capacitance element. The variable delay line having excellent high frequency characteristic which may be realized by such LC circuit ensures the maximum variable range of five folds and the maximum delay time of about 1 $\mu$s. However, since a delay time may be controlled respectively for the variable delay lines $15_1$–$15_5$, the delay time of the variable delay lines belonging to the aperture in respective timings can be controlled from the maximum value to minimum value in accordance with the aperture which gradually changes with time from the beginning of the reception. Accordingly, when the aperture is minimum in the beginning of reception, the delay time can be distributed to the minimum value from the maximum value within the range of such aperture. This condition is indicated by the curve $\tau 1$ in FIG. 2A. In the FIG. 2A, distribtion of delay time of aperture is indicated by plotting the aperture in the vertical direction and the delay time in the horizontal direction. Thereby, when the aperture is in the minimum condition, the focal distance can be set to extremely small value and the focusing can be made to the region near the surface of object. When the aperture is expanded, distribution of delay time can be determined adequately in the respective ranges of aperture and thereby the focusing can be made in accordance with respective apertures. For the maximum aperture, the focusing can also be made, for example, by setting distribution of delay time like the curve $\tau 2$. FIG. 2B indicates such changes of aperture and focusing and it can be understood therefrom that the focusing range can be expanded to the region near the surface of object to the deeper region.

While the present invention has been described with respect to a best mode thereof, it is to be understood that the present invention is not limited thereto in any way but covers any and all changes and modifications which will become possible within the scope of the claim.

What is claimed is:

1. A received ultrasonic phase matching circuit comprising variable attenuators which are provided respectively to a plurality of receiving channels forming a maximum aperture for reception of ultrasonic echoes and individually controlled, variable delay lines of the equal maximum delay time which are provided to a plurality of receiving channels forming the maximum aperture for reception of ultrasonic echoes and individually controlled and a beam steering means for adding and combining receiving signals respectively delayed by these variable delay lines, characterized in that a variable aperture is formed by said variable attenuators and distribution of delay times for focusing in the aperture is formed using only said variable delay lines belonging to said aperture.

* * * * *